US010578425B2

(12) United States Patent
Ezzelle et al.

(10) Patent No.: US 10,578,425 B2
(45) Date of Patent: Mar. 3, 2020

(54) FABRIC TEST SYSTEM AND METHOD

(71) Applicant: Czarnowski Display Service, Inc., Chicago, IL (US)

(72) Inventors: Larry Ezzelle, Acworth, GA (US); Jay Pryor, Winston, GA (US); Kirk Charles, Austell, GA (US); Craig Cochran, Atlanta, GA (US); Adam Ambrecht, Kennesaw, GA (US)

(73) Assignee: Czarnowski Display Service, Inc., Chicago, IL (US)

( * ) Notice: Subject to any disclaimer, the term of this patent is extended or adjusted under 35 U.S.C. 154(b) by 229 days.

(21) Appl. No.: 15/864,817

(22) Filed: Jan. 8, 2018

(65) Prior Publication Data

US 2019/0212126 A1  Jul. 11, 2019

(51) Int. Cl.
*G01B 5/26* (2006.01)
*G01B 11/03* (2006.01)
*G01B 11/00* (2006.01)
*G01N 21/88* (2006.01)
*G01M 5/00* (2006.01)
*G01N 33/36* (2006.01)

(52) U.S. Cl.
CPC ............ *G01B 11/03* (2013.01); *G01B 11/002* (2013.01); *G01M 5/00* (2013.01); *G01N 21/8803* (2013.01); *G01N 33/367* (2013.01)

(58) Field of Classification Search
CPC .................... G01N 21/8803; G01N 33/367
USPC ......................................... 33/1 BB, 121, 228
See application file for complete search history.

(56) References Cited

U.S. PATENT DOCUMENTS

| 2,674,888 | A | * | 4/1954 | Simonet | A61J 3/02 73/429 |
| 2,701,980 | A | * | 2/1955 | Abbott | G01N 33/367 356/238.1 |
| 2,707,415 | A | * | 5/1955 | Rooney, Jr. | G01N 21/8803 356/446 |
| 2,770,044 | A | * | 11/1956 | Wood | G01B 11/28 33/121 |
| 3,890,715 | A | * | 6/1975 | Kaplan | G01B 5/26 33/1 B |
| 4,464,841 | A | * | 8/1984 | McCay | G01B 5/02 33/1 BB |

(Continued)

*Primary Examiner* — George B Bennett
(74) *Attorney, Agent, or Firm* — Neal, Gerber & Eisenberg LLP

(57) ABSTRACT

Embodiments include a system for test fitting fabric, comprising a flat structure comprising a test surface defined by four sidewalls and an interface configured to attach the fabric to the test surface. The four sidewalls include a first sidewall and a second sidewall substantially perpendicular to the first sidewall. The test surface comprises a first adjustable dimension substantially parallel to the second sidewall and a second adjustable dimension substantially parallel to the first sidewall. The system also includes a user interface configured to receive one or more inputs for adjusting the first adjustable dimension and the second adjustable dimension; a first mechanism configured to, in response to the one or more inputs, automatically move the first sidewall to adjust the first adjustable dimension; and a second mechanism configured to, in response to the one or more inputs, automatically move the second sidewall to adjust the second adjustable dimension.

19 Claims, 13 Drawing Sheets

(56) References Cited

U.S. PATENT DOCUMENTS

| | | | | |
|---|---|---|---|---|
| 4,466,192 A * | 8/1984 | Ager | ........................ | B41B 23/00 |
| | | | | 33/1 B |
| 4,719,704 A * | 1/1988 | Hogg | ..................... | G01B 5/207 |
| | | | | 33/288 |
| 5,564,169 A * | 10/1996 | Willauer, Jr. | .......... | D06C 23/04 |
| | | | | 26/69 R |
| 6,219,930 B1 * | 4/2001 | Reid | ........................ | G01B 3/14 |
| | | | | 33/1 BB |
| 7,584,587 B2 * | 9/2009 | Ouellette | ............ | E04F 13/0889 |
| | | | | 33/646 |
| 2003/0189968 A1 * | 10/2003 | Lu | ........................ | G01N 33/367 |
| | | | | 374/45 |
| 2008/0163524 A1 * | 7/2008 | Broehl | ..................... | A47G 1/06 |
| | | | | 40/299.01 |
| 2011/0098539 A1 * | 4/2011 | Estocado | ............. | A61B 5/1072 |
| | | | | 600/300 |
| 2016/0178535 A1 * | 6/2016 | Houston | .............. | G01N 21/958 |
| | | | | 356/239.1 |

\* cited by examiner

FABRIC TEST SYSTEM AND METHOD

BACKGROUND

The description that follows relates generally to systems and methods for test fitting large sheets of fabric, or other pieces made of a flexible material. The flexible pieces may be, for example, signs, banners, flags, or panels configured to be mounted on a frame or other support structure, suspended from a rod or on a pole, or otherwise displayed.

As will be appreciated, when using a flexible material for signage, it is desirable to hold the material as taut as possible, e.g., like the skin of a drum, so that the content printed on the sign is legible and/or clearly displayed. Often times, fabric signs are test fitted prior to installation to ensure that the fabric piece is properly sized and cut for the intended display space. However, for extremely large pieces (e.g., banners for display on the side of a building), it can be difficult to find a site that is large enough to properly test fit the piece. Moreover, in situations where each sign can be customized to match specific dimensions, it can be difficult to find a single testing facility that can accommodate and provide precisely sized test frames for test fitting fabric pieces of various sizes (e.g., from the small to the very large), shapes (e.g., rectangular, square, etc.), and orientations (e.g., horizontal, vertical, etc.).

SUMMARY

Improved systems and methods for test fitting fabrics or other flexible materials are provided herein. One exemplary embodiment provides a system for test fitting fabric, comprising a flat structure comprising a test surface defined by four sidewalls and an interface configured to attach the fabric to the test surface. The four sidewalls include a first sidewall and a second sidewall substantially perpendicular to the first sidewall. The test surface comprises a first adjustable dimension substantially parallel to the second sidewall and a second adjustable dimension substantially parallel to the first sidewall. The system also includes a user interface configured to receive one or more inputs for adjusting the first adjustable dimension and the second adjustable dimension; a first mechanism configured to, in response to the one or more inputs, automatically move the first sidewall to adjust the first adjustable dimension; and a second mechanism configured to, in response to the one or more inputs, automatically move the second sidewall to adjust the second adjustable dimension.

Another example embodiment includes a method of test fitting fabric on a flat structure comprising a test surface, the flat structure being included in a system comprising a processor and a user interface, the method comprising receiving, via the user interface, dimensions associated with a test piece; generating, using the processor, instructions for adjusting one or more dimensions of the test surface based on the received dimensions; and providing a first one of the instructions to a first mechanism coupled to a first moveable portion of the flat structure for causing automatic adjustment of a first dimension of the test surface.

A better understanding of the invention will be obtained from the following detailed descriptions and accompanying drawings, which set forth illustrative embodiments that are indicative of the various ways in which the principals of the invention may be employed.

Figure 1:
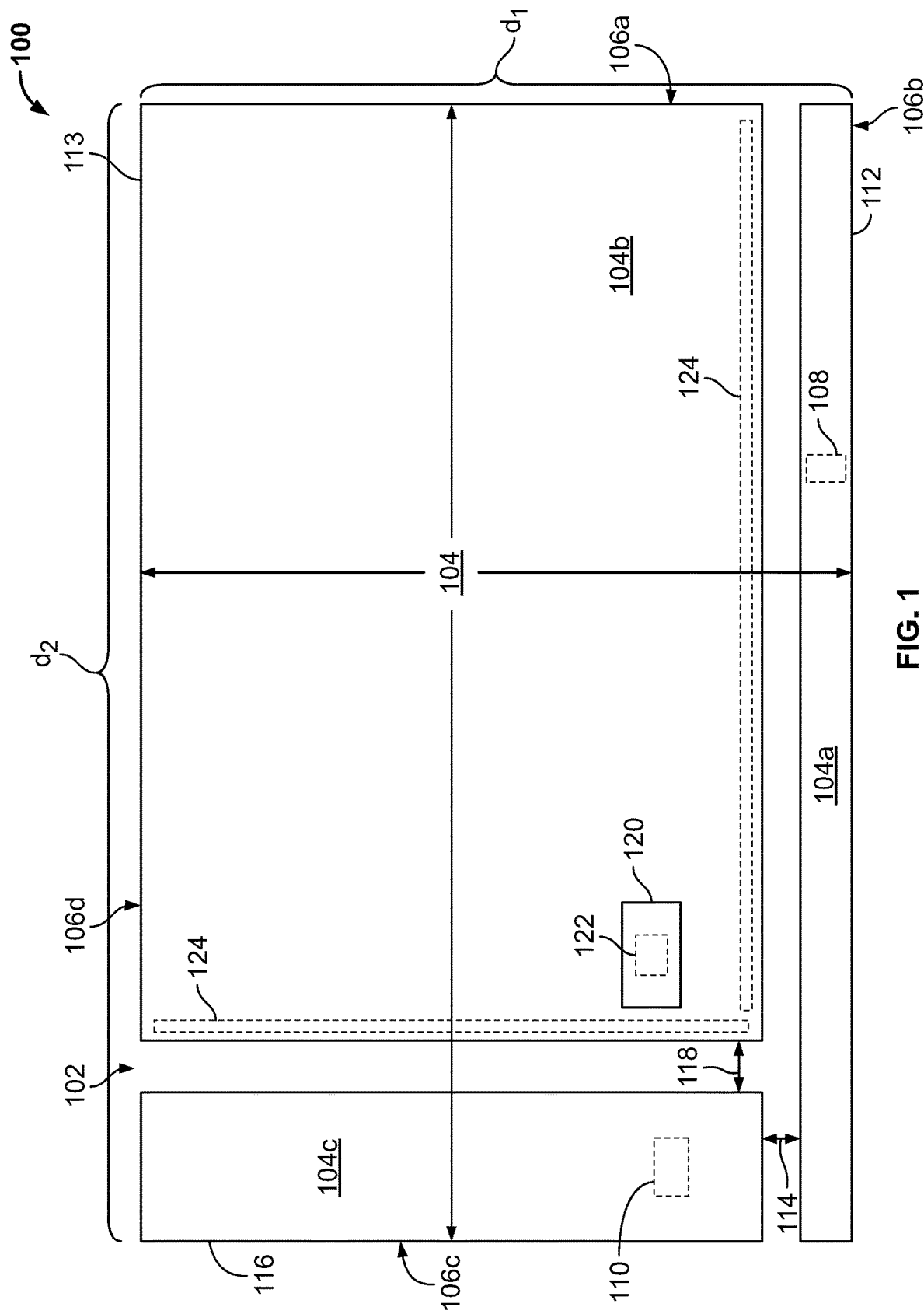
FIG. 1 is a block diagram of an exemplary test fitting system, in accordance with embodiments.

Illustrative and exemplary embodiments of the invention are described in further detail below with reference to and in conjunction with the figures.

DETAILED DESCRIPTION

The description that follows describes, illustrates and exemplifies one or more embodiments of the invention in accordance with its principles. This description is not provided to limit the invention to the embodiment(s) described herein, but rather to explain and teach the principles of the invention in order to enable one of ordinary skill in the art to understand these principles and, with that understanding, be able to apply them to practice not only the embodiment(s) described herein, but also any other embodiment that may come to mind in accordance with these principles. The scope of the invention is intended to cover all such embodiments that may fall within the scope of the appended claims, either literally or under the doctrine of equivalents.

It should be noted that in the description and drawings, like or substantially similar elements may be labeled with the same reference numerals. However, sometimes these elements may be labeled with differing numbers or serial numbers in cases where such labeling facilitates a more clear description. Additionally, the drawings set forth herein are not necessarily drawn to scale, and in some instances proportions may have been exaggerated to more clearly depict certain features. Also, some of the drawings include partial views that have select parts removed for the sake of clarity with respect to the depicted portions. As stated above, this specification is intended to be taken as a whole and interpreted in accordance with the principles of the invention as taught herein and understood by one of ordinary skill in the art.

In this application, the use of the disjunctive is intended to include the conjunctive. The use of definite or indefinite articles is not intended to indicate cardinality. In particular, a reference to "the" object or "a" and "an" object is intended to denote also one of a possible plurality of such objects.

Figure 2:
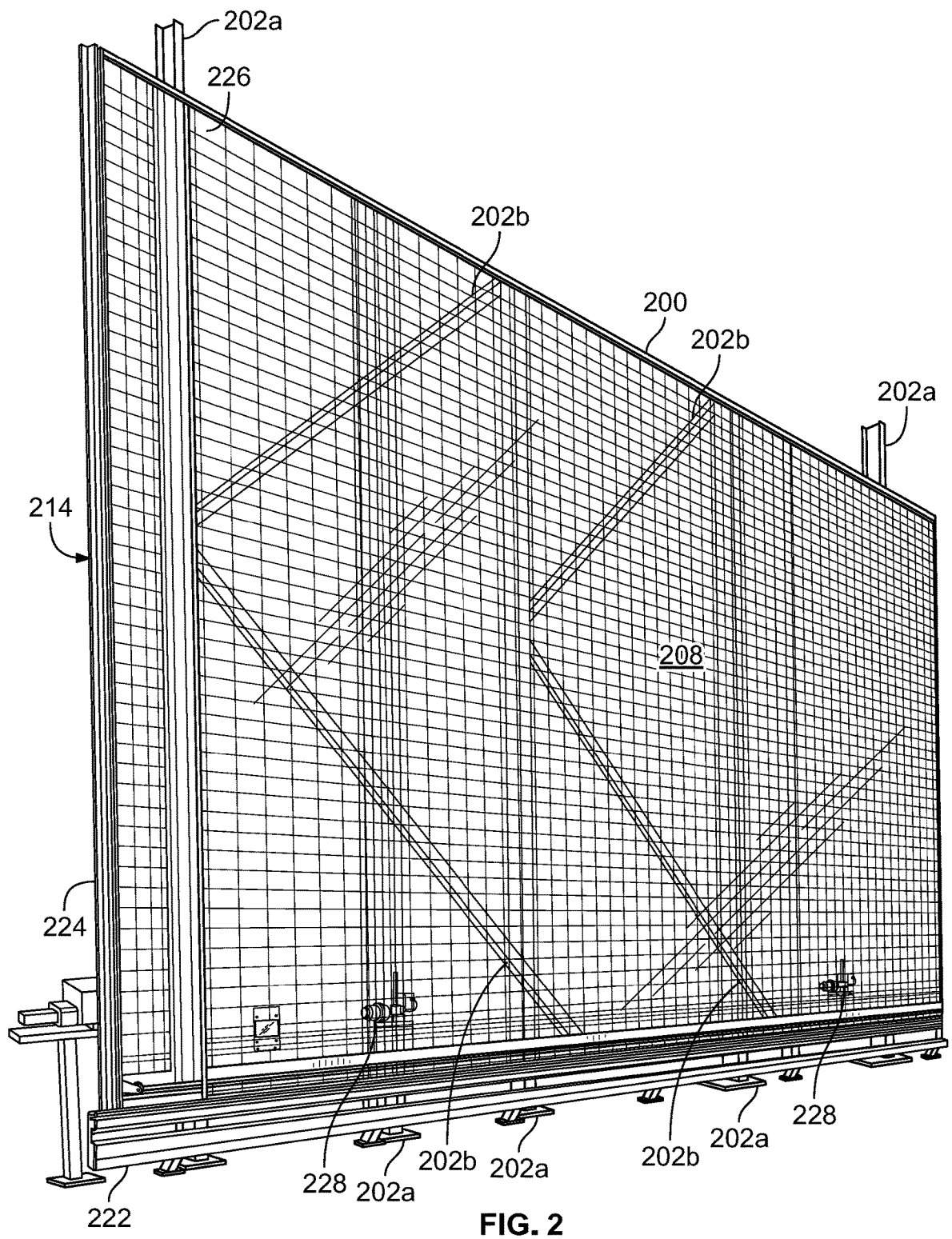
FIG. 2 is a front perspective view of an example fabric test wall, in accordance with embodiments.

FIG. 1 depicts an example test fitting system 100 in accordance with embodiments. The test fitting system 100 includes a flat structure 102 configured to receive a fabric piece or other flexible material for testing a fit (e.g., size, shape, stretch, presentation, readability, etc.) of the piece. In some embodiments, the flat structure 102 is configured to be a wall, or as a vertical or upright structure. For example, FIGS. 2-10 depict an exemplary flat structure 200 that is arranged as a wall for test fitting fabric (also referred to herein as a "fabric test wall"). As shown in FIG. 2, the fabric test wall 200 is held upright by a frame 202 that is comprised of various beams 202a and trusses 202b coupled to, or supported by, the ceiling, the floor, and/or one or more walls of the testing facility. In other embodiments, the flat structure 102 may be configured as a horizontal structure (e.g., a floor or table space) for test fitting fabric pieces. The flat structure 102 may be made of any suitable material that is strong and sturdy enough to handle the size and weight of the test pieces but also lightweight to minimize the bulkiness of the overall structure. In the illustrated embodiments, the fabric test wall 200 is made of a clear, acrylic material.

Figure 3:
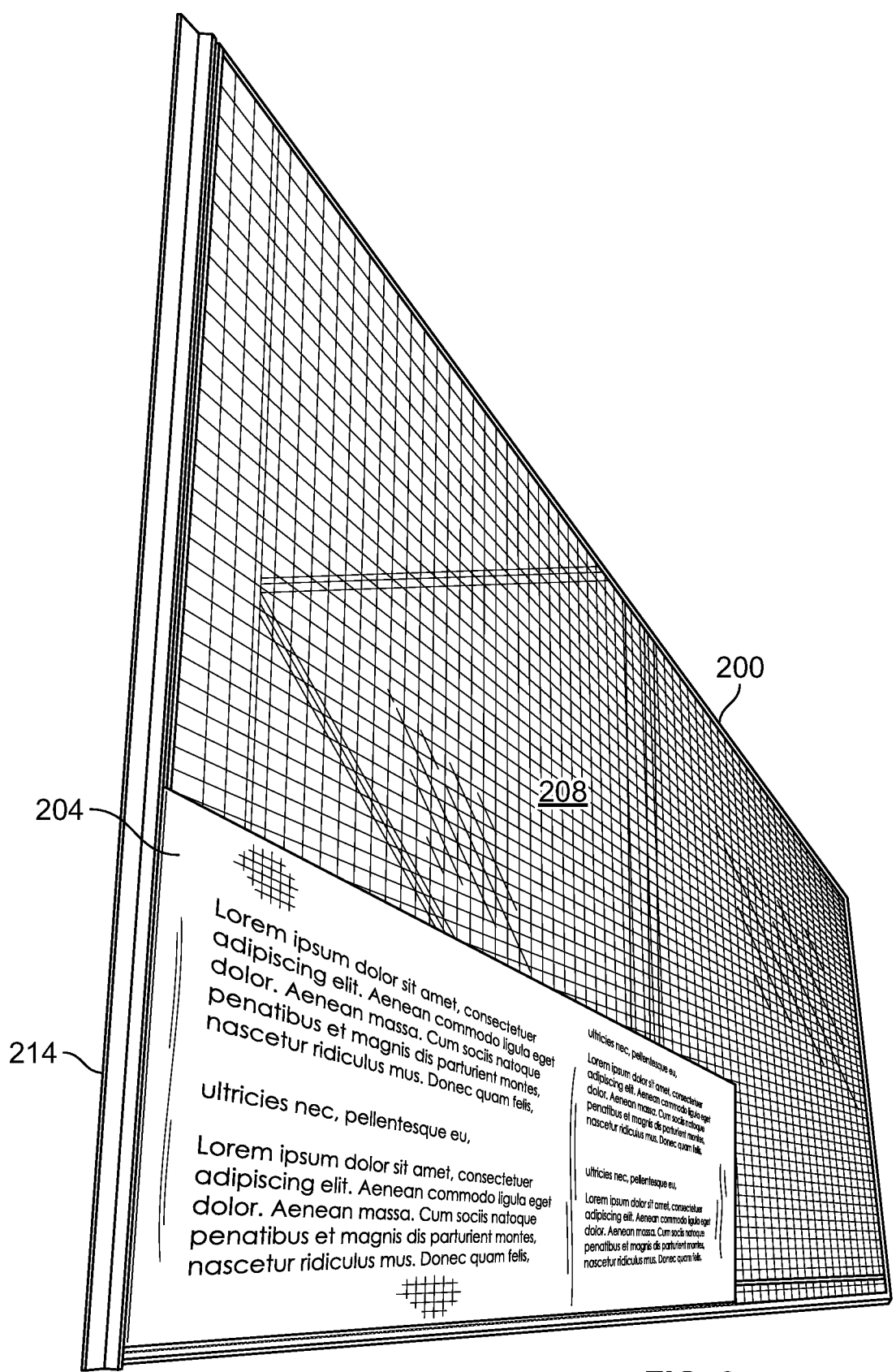
FIG. 3 illustrates a first example fabric attached to the wall shown in FIG. 2, in accordance with embodiments.
Figure 4A:
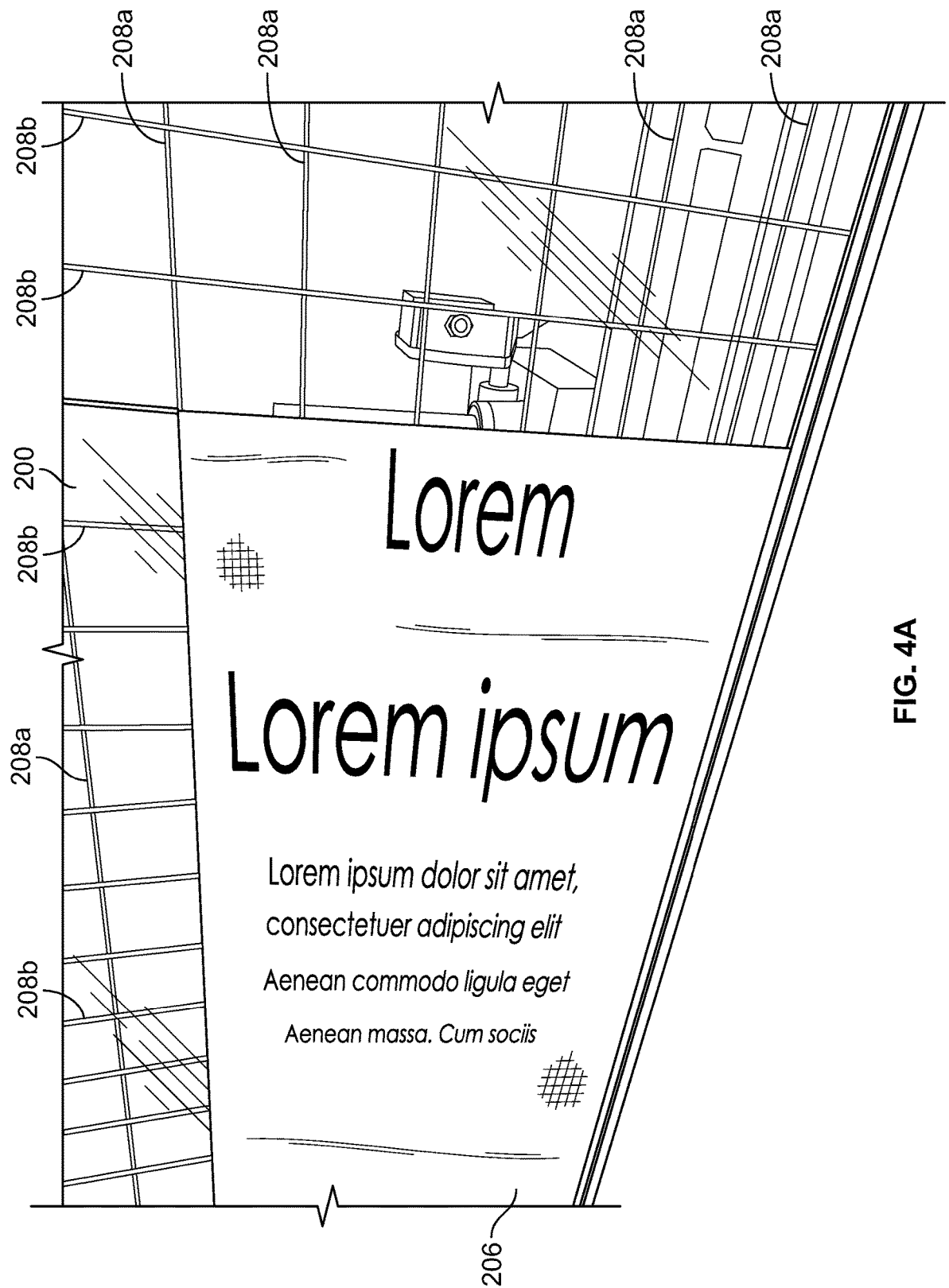
FIG. 4A illustrates a second example fabric attached to the wall shown in FIG. 2, in accordance with embodiments.
Figure 4B:
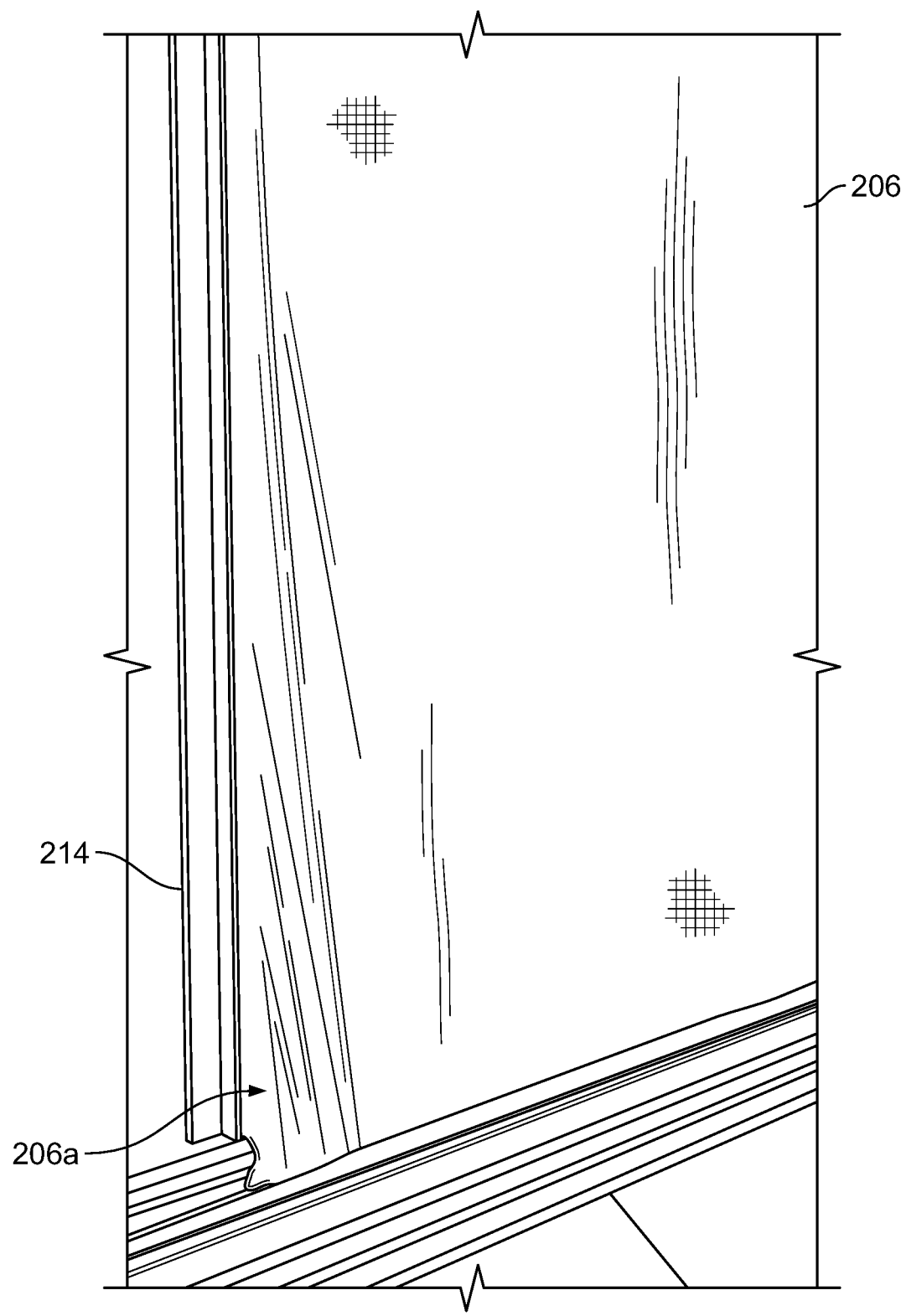
FIG. 4B is a close-up view of a bottom left edge of the fabric shown in FIG. 4A, in accordance with embodiments.

Referring back to FIG. 2, in embodiments, the fabric test wall 200 can be made very large in size in order to accommodate even the largest fabric pieces. For example, one embodiment of the fabric test wall 200 is approximately 25 feet tall by 40 feet wide. The fabric test wall 200 can also be configured to receive the test piece in various orientations in order to be able to accommodate all types of pieces, including different sized banners and signs. For example, FIG. 3 shows the fabric test wall 200 with a first fabric sign 204 attached to the wall 200 in a vertical or upright orientation, while FIGS. 4A and 4B shows the fabric test wall 200 with a second fabric sign 206 attached to the wall 200 in a horizontal or sideways orientation. The dimensions or type of a given test piece may determine how the piece is attached to, or tested on, the wall 200. For example, while it may be preferable to test most signs in the vertical orientation for legibility reasons and to mimic the intended display position, oblong pieces may be easier to test in the horizontal orientation due to improved handling and maneuverability.

Referring back to FIG. 1, the flat structure 102 comprises a test surface 104 and four sidewalls 106a, 106b (also referred to herein as a "first sidewall"), 106c (also referred to herein as a "second sidewall"), and 106d. As shown, the sidewalls 106 substantially define the outer boundaries of the test surface 104. In embodiments, the test surface 104 constitutes the surface area of the flat structure 102 that is capable of, or configured for, receiving a fabric piece for testing a fit of the fabric. The flat structure 102 further includes an attachment interface configured to receive and retain the fabric piece against the test surface 104 during test fitting. In embodiments, the attachment interface is made up of one or more components that are embedded into, included on, and/or coupled to the test surface 104 and are configured to receive one or more edges of the test piece. The components of the attachment interface can be configured to create a test frame that mimics the attachment mechanism(s) that will be used to hang or display the fabric sign at its intended display location, so that any errors in the fit of the fabric piece can be identified prior to delivery and/or installation. For example, one or more of the components included in the attachment interface may be the same as, or substantially similar to, the attachment mechanism(s) (e.g., frame, track, rail, etc.) at the intended display site (such as, e.g., F-track 214 shown in FIG. 6 or keder rail 220 shown in FIG. 8A).

Referring now to FIG. 4A, shown is a close-up view of a first component of an exemplary attachment interface included on the fabric test wall 200 for receiving one or more edges of a test piece, in accordance with embodiments. As shown, the first component is a grid-like interface 208 formed from a plurality of horizontal channels 208a intersecting with a plurality of vertical channels 208b. Each channel 208a, 208b includes a groove or slot in the wall 200 that is configured to receive, or is capable of receiving, an edge of the fabric piece being test fitted. In some embodiments, the channels 208a and 208b include an attachment structure configured to facilitate attachment to, or retention of, a test piece. For example, each of the channels 208a and 208b may have a tapered structure that is wide at the opening and narrows towards the back or inside wall of the channel 208a, 208b. The wider opening may make it easier to insert a test piece edge into the channel 208a, 208b, and the narrowing structure may be configured to securely grip and adhere to the fabric edge within the channel.

Figure 5A:
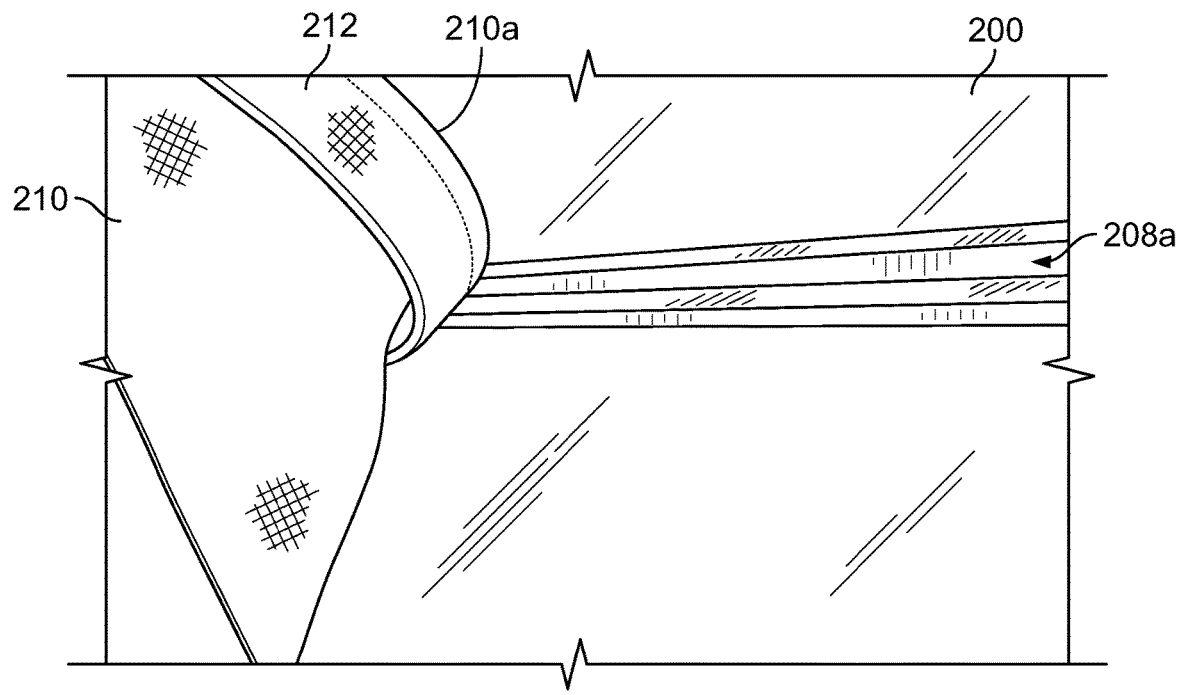
FIGS. 5A and 5B are close up views of the fabric test wall of FIG. 2 and show installation of a first edge of a fabric piece into an exemplary attachment interface, in accordance with embodiments.
Figure 5B:
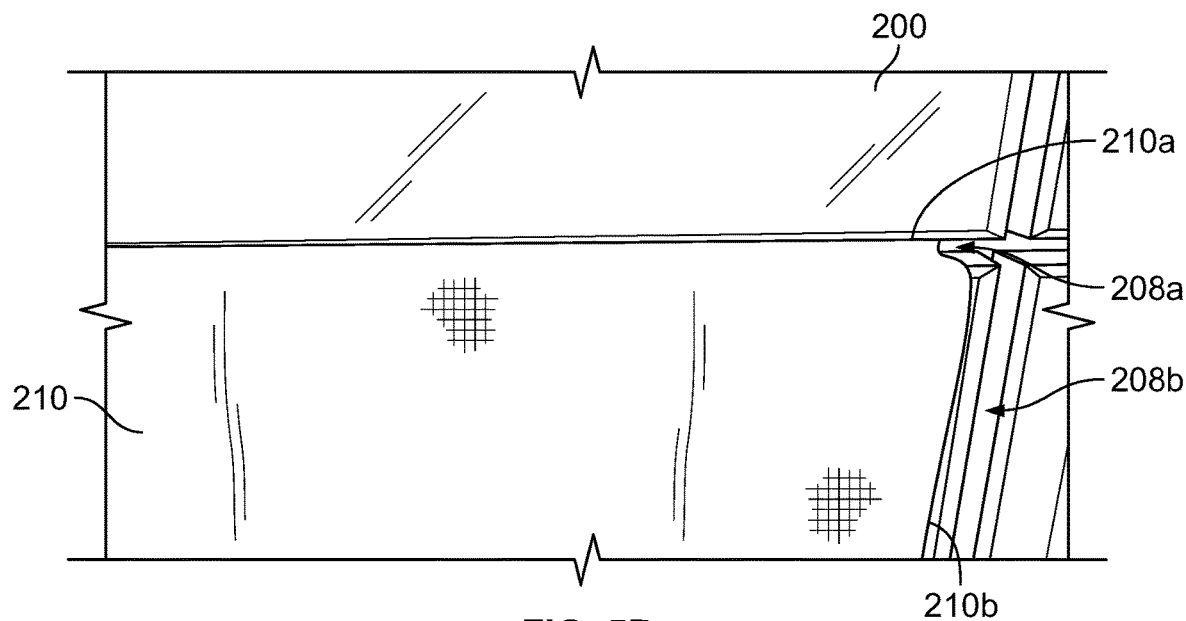

In some embodiments, the channels 208a, 208b are also configured to receive an attachment mechanism coupled to the edge of the fabric piece. For example, FIG. 5A shows a close up view of the fabric test wall 200, one of the horizontal channels 208a, and a test piece 210 comprising a silicon gasket 212 sewn or attached to an underside of a horizontal edge 210a of the test piece 210. FIG. 5B shows the horizontal edge 210a of the test piece 210 fully inserted into or coupled to the horizontal channel 208a, so that the test piece 210 hangs from the channel 208a. Though not shown, the vertical channel 208b may similarly engage the vertical edge 210b of the test piece 210 in order to securely attach another side of the piece 210 to the wall 200. In embodiments, each of the channels 208a, 208b may be sized and shaped to receive the silicon gasket 212 through the opening of the channel and retain the silicon gasket 212 against an interior surface of the channel. For example, the material used to form the channels 208a and 208b and/or the fabric test wall 200 may be selected so that the silicon gasket 212 easily grips or latches onto the interior walls of the channels 208a, 208b. In some cases, a coating may be applied within the channels 208a, 208b to increase the grippiness or stickiness of the walls that form the tapered structure within each channel.

Figure 6:
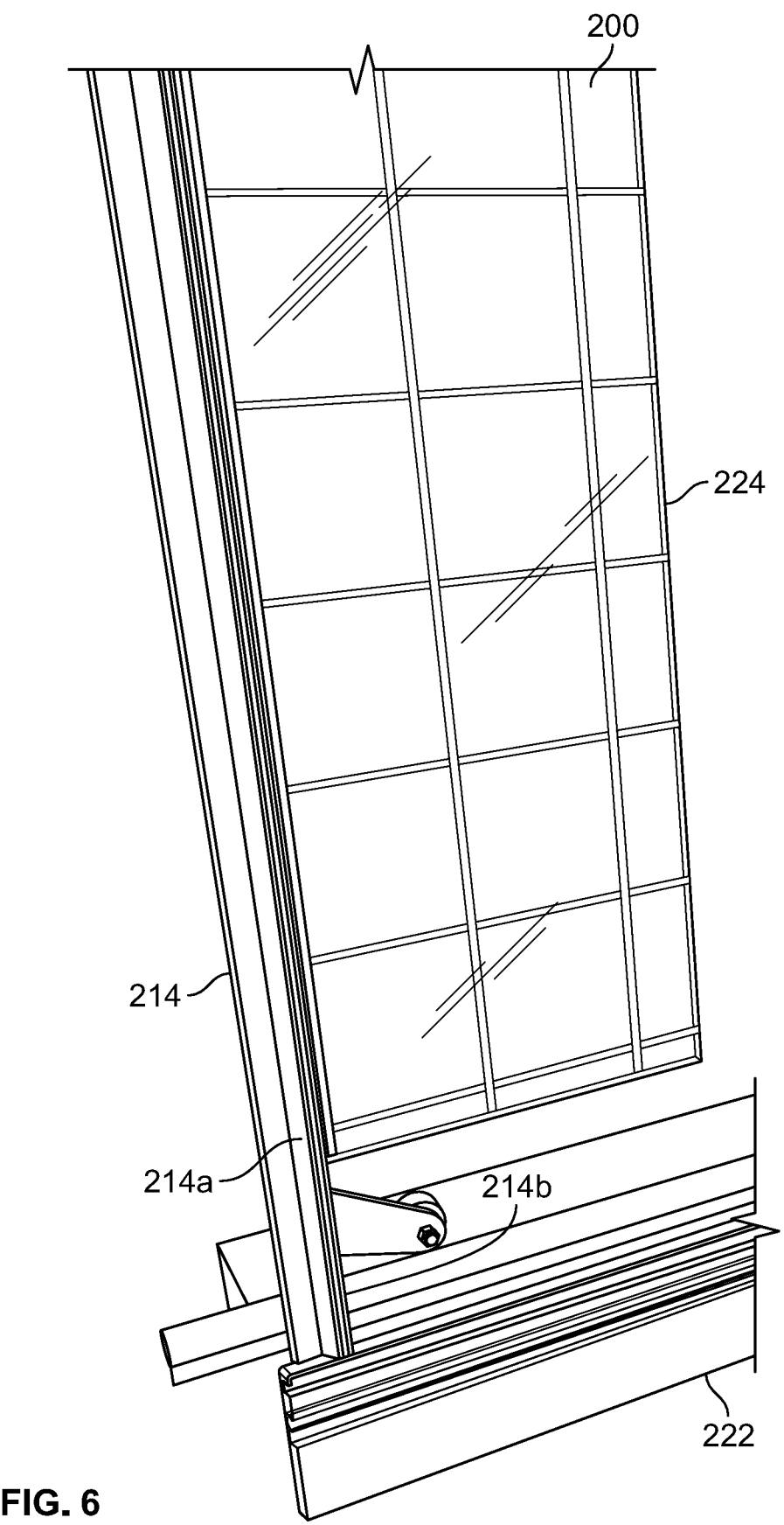
FIG. 6 is a close-up view of an exemplary vertical attachment interface included on the fabric test wall of FIG. 2 for attaching a fabric piece to the wall, in accordance with embodiments.
Figure 7A:
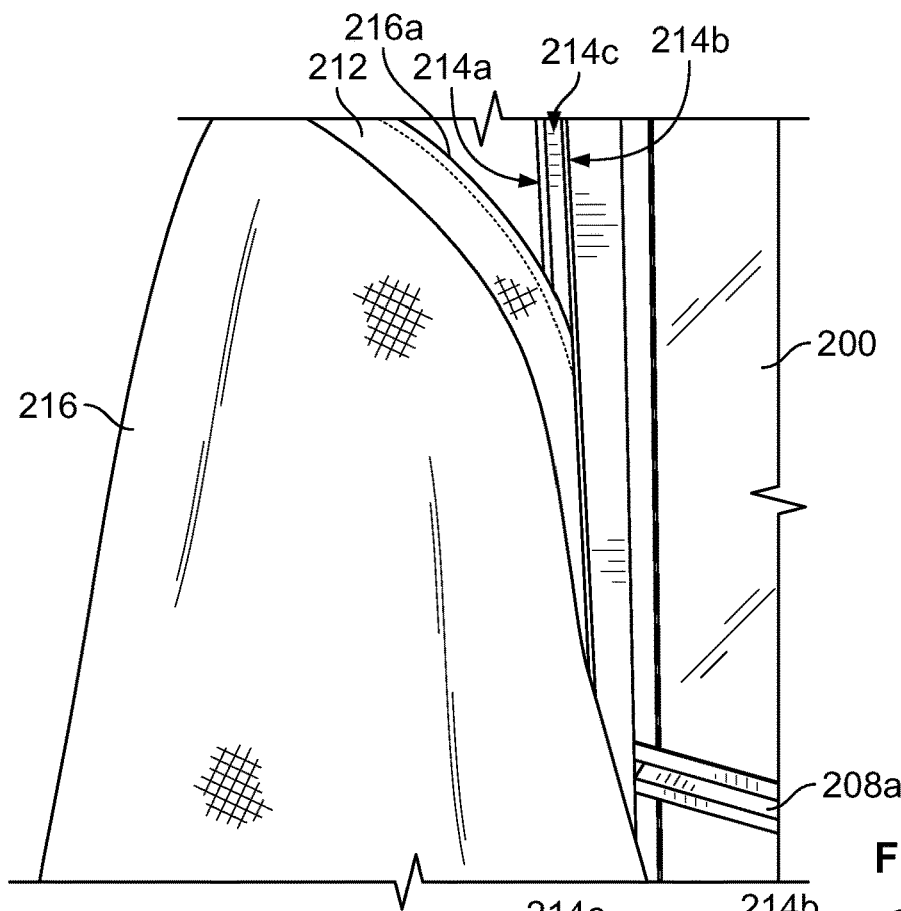
FIGS. 7A and 7B are close-up views of the vertical attachment interface of FIG. 6 and installation of a second edge of a fabric piece into said interface, in accordance with embodiments.
Figure 7B:
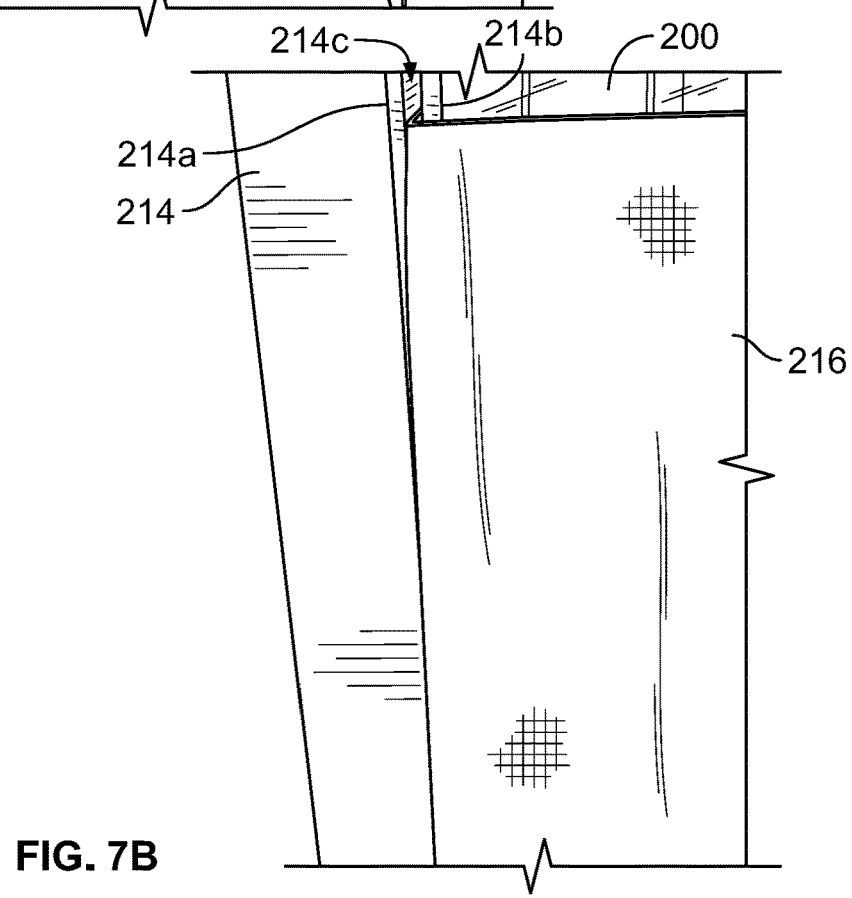

Referring now to FIG. 6, show is a close-up view of a second component of the exemplary attachment interface included on the fabric test wall 200 for receiving an edge of a test piece, in accordance with embodiments. As illustrated, the second component can be a vertical track 214 coupled to a left sidewall of the wall 200 (e.g., sidewall 106c shown in FIG. 1), extending vertically along substantially the entire left sidewall. FIGS. 7A and 7B are close up views of the fabric test wall 200 showing a test piece 216 being coupled to the track 214. In embodiments, the track 214 can be configured to securely receive a left edge 216a of the test piece 216, including any silicon gasket 212 or other attachment mechanism attached to said edge 216a, as shown in FIG. 7A. In the illustrated embodiment, the track 214 has an "F-track" shape that is formed by two parallel walls 214a and 214b extending outwardly from, or perpendicular to, the wall 200. In embodiments, the F-track 214 may be an extruded piece of aluminum, and a distance between the two parallel walls 214a and 214b may be selected so as to form a narrow slot or channel 214c having an inside dimension that is sized to fit and retain the edge 216 of the test piece, as shown in FIG. 7A. For example, most of the fabric signs being test fitted on the wall 200 may include a standard-sized strip of silicon material that is attached along the edges of each sign. Accordingly, the F-track channel 214c may be sized to fit sign edges having this silicon gasket. In some cases, the F-track 214 may be similar to, or the same as, the attachment interface used to display fabric signs at intended display location. For example, one or more F-tracks may be cut to length depending on the size of the fabric sign and attached to a wall or a side of a building for the purpose of displaying fabric banners or signs thereon.

Figure 8A:
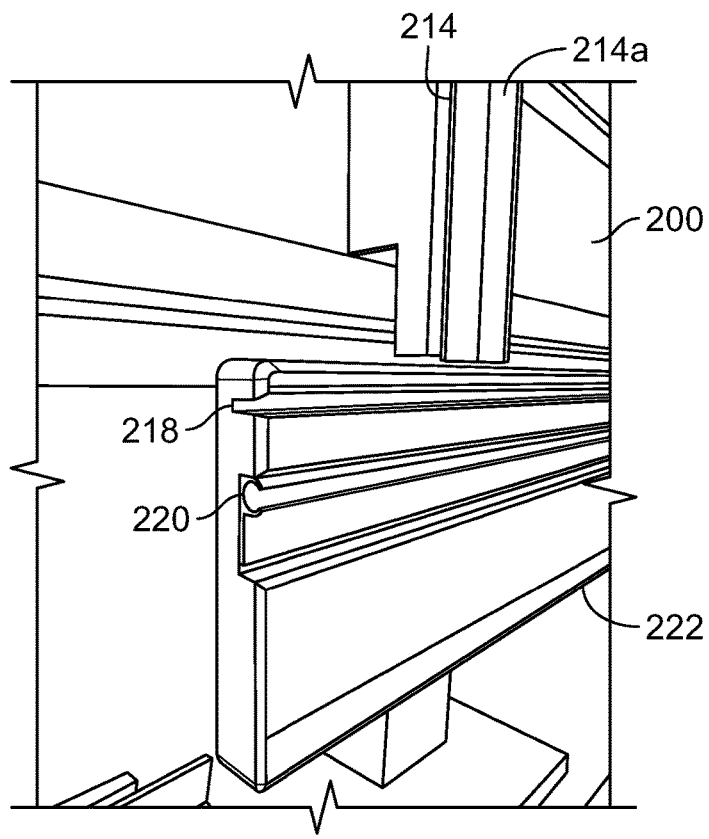
FIGS. 8A and 8B are close-up views of a horizontal attachment interface included on the fabric test wall of FIG. 2 for attaching a third edge of a fabric piece to the wall, in accordance with embodiments.
Figure 8B:
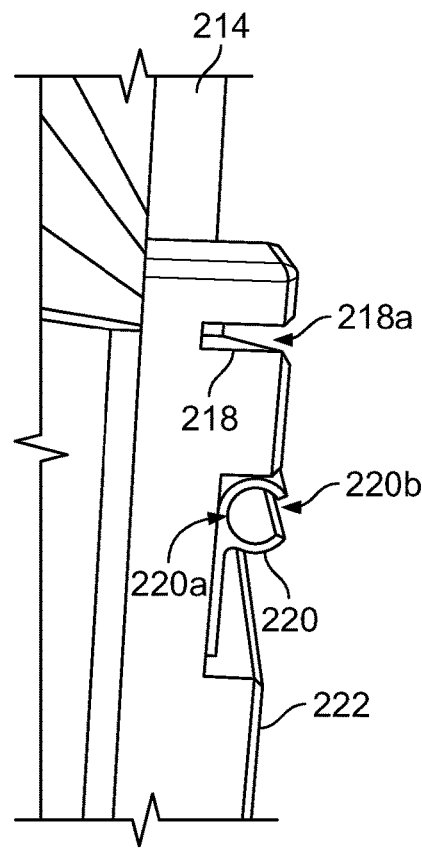

FIGS. 8A and 8B depict a third component of the exemplary attachment interface included on the fabric test wall 200 for receiving an edge of a test piece, in accordance with embodiments. The third component includes one or more horizontal channels coupled to, or included on, a bottom sidewall of the wall 200 (e.g., first sidewall 106b), extending horizontally along substantially the entire bottom sidewall and configured to receive a bottom edge, or downwards-facing edge, of a test piece. As shown, in some embodiments, the third component includes two channels for receiving two different types of edges: a first bottom channel 218 configured to receive a test piece edge having a silicon gasket, or other attachment mechanism, attached thereto (e.g., similar the edge 216a shown in FIG. 7A), and a second bottom channel 220 configured to receive a keder or other similar product having a tubular or cylindrical core attached to a fabric. As an example, FIG. 8A shows a front perspective view of two exemplary bottom channels 218 and 220, and FIG. 8B shows a close up, side view of the two bottom channels 218 and 220.

In the illustrated embodiment, the first channel 218 is substantially similar to the channels 208a and 208b that make up the grid 208 for receiving one or more edges with a silicon gasket attached thereto (e.g., as shown in FIGS. 5A and 5B). For example, like the channels of the grid 208, the first bottom channel 218 includes a groove or slot 218a that is configured to receive and securely hold the bottom edge of a given test piece. In some cases, the first bottom channel 218 may include top and bottom walls that slant towards each other and meet at an inner back wall, so as to create a tapered slot for securing the edge of the test piece within the slot 218a. For example, the first bottom channel 218 may be structured so that an outer face or opening is wide enough to easily receive a test piece edge inserted therein, and the back wall is narrow enough to cause the test piece edge to be gripped or clamped between the top and bottom walls. When in this position, the silicon gasket attached to the underside of test piece edge is pressed against and interfaces with the bottom wall of the first bottom channel 218, thus preventing the test piece edge from slipping out of the channel 218.

As also shown in FIG. 8B, the second bottom channel 220 includes a rounded or circular rail 220a for receiving a cylindrical core of the keder product and an opening 220b within that rail 220a for allowing the fabric attached to the keder core to exit or extend therethrough. In embodiments, a diameter of the second bottom channel 220 can be sized and shaped to fit one or more type(s) of keder expected to be test fitted on the fabric test wall 200. In some embodiments, the dimensions of the second bottom channel 220 can be selected so that any size keder, big or small, can fit within the circular rail 220a without fall out through the fabric opening 220b during testing. For example, the circular rail 220a may be configured to have a diameter that is at least equal to the diameter of the largest type of keder (e.g., 15 mm), and the fabric opening 220b may be configured to have a height that is smaller than the diameter of the smallest type of keder (e.g., 4 mm). As will be appreciated, due to the location of the keder rail 220 at the bottom of the fabric test wall 200, any keder-style sign or banner will be loaded top side down in the vertical orientation, so that the top side of the keder is attached to the keder rail 220, the right side of the keder is attached to the vertical track 214, and the left and bottom sides of the keder are attached to corresponding channels of the grid 208.

Referring back to FIG. 4B, shown is a close up view of a bottom, left corner of the fabric test wall 200 and a depiction of an exemplary fabric testing scenario. In the illustrated example, the test piece (i.e. the second sign 206) attached to the fabric test wall 200 has an imperfect fit that is evidenced by the excess fabric bunching in the bottom left corner 206a of the sign 206. This bunching may have been caused by imprecise cutting of the fabric, errors in calculating the stretch of the fabric material, improper finishing of the piece, and/or other factors, as will be appreciated by those skilled in the art. Other signs of an imperfect fit may include a gap between the edge of the test piece and a corresponding sidewall of the fabric test wall 200, a fabric edge that overlaps or extends past a corresponding sidewall of the wall 200, and/or a fabric piece that is over-stretched or pulled too tightly. Upon discovering an imperfect fit, the test piece may be sent back to the manufacturing facility for correction and/or remaking.

Figure 9:
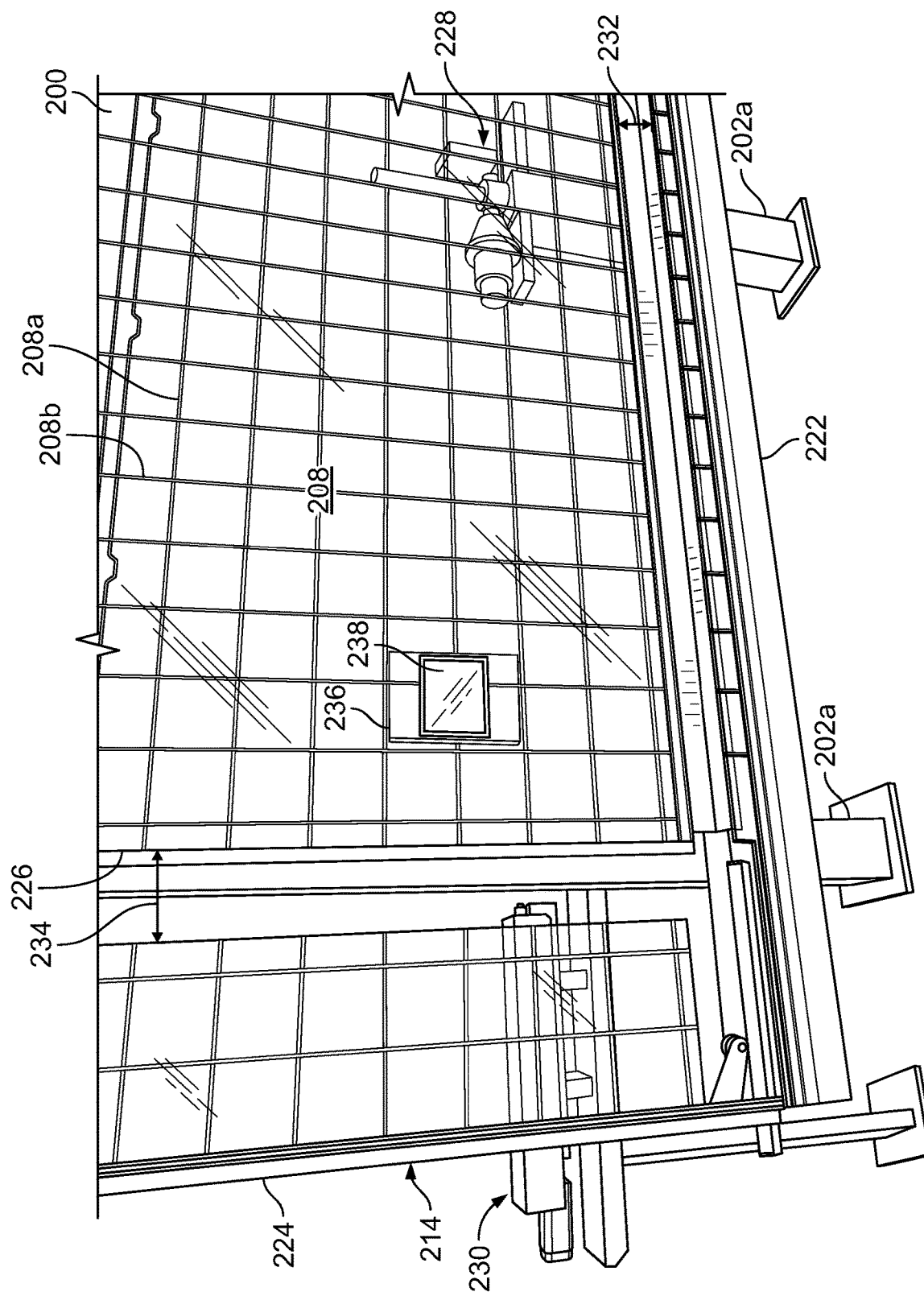
FIG. 9 is a close-up, front perspective view of a lower left section of the wall shown in FIG. 2, showing various components of the wall in more detail, in accordance with embodiments.

Referring back to FIG. 4A, and now also to FIG. 9, according to embodiments, the attachment interface grid 208 can be formed by positioning the horizontal channels 208a at predetermined distances apart (e.g., every 6 inches), and similarly positioning the vertical channels 208b at predetermined distances apart (e.g., every 6 inches). In embodiments, the distance between adjacent horizontal channels 208a is substantially equal to the distance between adjacent vertical channels 208b, and the horizontal channels 208a are substantially perpendicular to the vertical channels 208b, as shown. This grid-like configuration of the interface 208 allows the fabric test wall 200 to create test frames of various sizes and/or accommodate test pieces of various sizes, so long as the dimensions of the frame or piece are exact increments or multiples of the distance between adjacent channels (e.g., multiples of 6 inches).

Figure 11:
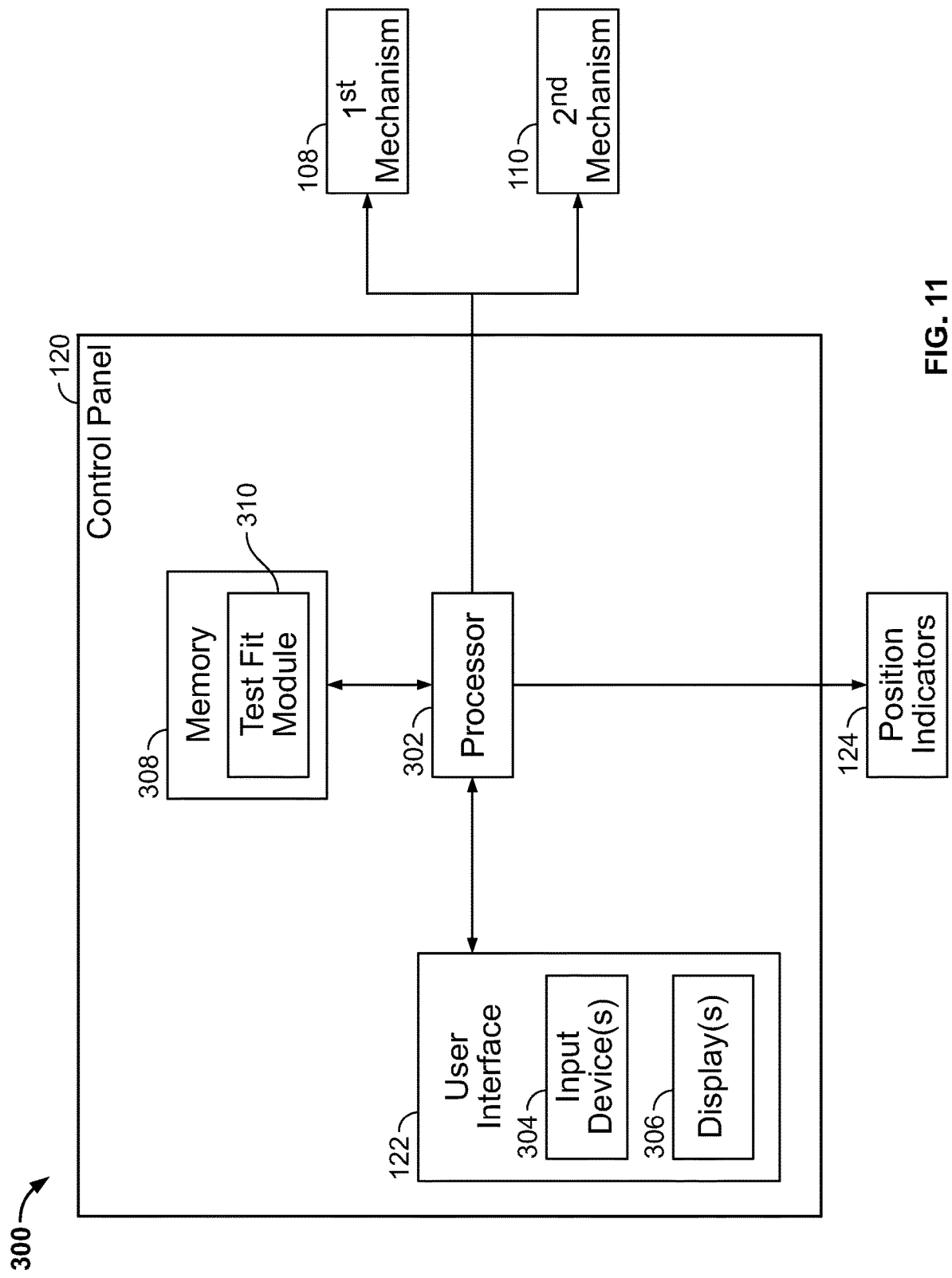
FIG. 11 is a block diagram of an example system for controlling the test fitting system of FIG. 1, in accordance with embodiments.

In embodiments, the test fitting system 100 and/or the fabric test wall 200 further includes a test surface adjustment system configured to adjust a size (e.g., height and width) of the test surface 104 to accommodate test frame or pieces with dimensions that fall between, for example, two adjacent horizontal channels 208a and/or two adjacent vertical channels 208b. As an example, FIG. 11 is a block diagram of an exemplary test surface adjustment system 300 that may be included in the test fitting system 100 for automatically adjusting the dimensions of the test surface 104 in order to provide more precise test frames. In some embodiments, the test surface adjustment system 300 may be configured to adjust the length and/or width dimensions of the test surface 104 by as little as approximately 1/100 of an inch and up to approximately 6 inches in order to more precisely match the attachment interface of the test surface 104 to the dimensions of the test frame or piece.

As shown in FIG. 1, the test surface 104 can include a first adjustable dimension $d_1$ that extends vertically over the test surface 104 of the flat structure 102, namely from the first sidewall 106b to its opposing sidewall 106d, and a second adjustable dimension $d_2$ that extends horizontally across the test surface 104, namely from the second sidewall 106c to its opposing sidewall 106a. According to embodiments, the test surface adjustment system 300 can include a first mechanism 108 for adjusting the first adjustable dimension $d_1$ or an overall length of the test surface 104, or more specifically, the length of the second sidewall 106c, and a second mechanism 110 for adjusting the second adjustable dimension $d_2$ or an overall width of the test surface 104, or more specifically, the width of the first sidewall 106b.

The test surface 104 can be divided into separate sections with at least one of the test surface sections being provided on a moveable piece of the flat structure 102 in order to provide fine-tunable test surface dimensions. For example, as shown in FIG. 1, the test surface 104 can include a first portion 104a comprising a horizontal strip of the test surface 104 along the first or bottom sidewall 106b, a second or central portion 104b comprising a majority of the test surface 104, and a third portion 104c comprising a vertical strip of the test surface 104 along the second or left sidewall 106c. At least one of the first portion 104a, the second portion 104b, and the third portion 104c of the test surface 104 can be moved relative to the remaining portions of the test surface 104 in order to allow adjustments to the overall length and/or width of the test surface 104 and to the spacing between the portions of the test surface 104. In the illustrated embodiment, the first portion 104a and the third portion 104c are moveable relative to the central portion 104b, which remains fixed in place. In other embodiments, the central portion 104b may be moved vertically and/or horizontally while the first portion 104a and/or the third portion 104c remain fixed in place.

As shown in FIG. 1, in order to make vertical size adjustments to the test surface 104, the flat structure 102 can include a first moveable member 112 that comprises the first or bottom sidewall 106b and the first portion 104a of the test surface 104. The flat structure 102 further includes a main wall 113 that includes the top sidewall 106d and the right sidewall 106a, as well as the second portion 104b of the test surface 104. The first mechanism 108 of the test surface adjustment system can be configured to vertically move the first moveable member 112, and the first sidewall 106b included therein, relative to the main wall 113, and the top sidewall 106d included therein, in order to adjust the first adjustable dimension $d_1$ of the test surface 104. The main wall 113 can remain fixed in place while the first moveable member 108 moves vertically, towards or away from the main wall 113.

As shown in FIG. 1, as the first moveable member 112 moves away from the main wall 113, a first gap 114 forms between the first moveable member 112 and the main wall 113. This increases the first adjustable dimension $d_1$ of the test surface 104 by the height of the first gap 114. In such cases, the first gap 114 forms part of the test surface 104 and may constitute the "adjustable" portion of the first adjustable dimension $d_1$. Further, placing the first gap 114 between the first portion 104a and the second portion 104b of the test surface 104 allows the test surface 104, or the attachment interface included thereon, to create test frames, or receive test pieces, with length-wise dimensions that are not exact multiples of the grid size (e.g., 6 inches). The first gap 114 may be minimized, or eliminated, by positioning the first moveable member 112 adjacent to, or flush with, the main wall 113. In one example embodiment, a height of the first gap 114 may be adjustable between zero and up to approximately 6 inches.

Likewise, in order to make horizontal size adjustments to the test surface 104, the flat structure 102 further includes a second moveable member 116 that comprises the second sidewall 106c of the flat structure 102 and a third portion 104c of the test surface 104. The second mechanism 110 of the test surface adjustment system can be configured to horizontally move the second moveable member 116, and the second sidewall 106c included therein, relative to the main wall 113, in order to adjust the second adjustable dimension $d_2$ of the test surface 104. In embodiments, the main wall 113 can remain fixed in place while the second moveable member 116 moves horizontally, towards or away from the main wall 113.

As shown in FIG. 1, as the second moveable member 116 moves away from the main wall 113, a second gap 118 forms between the second moveable member 116 and the main wall 113. This increases the second adjustable dimension $d_2$ of the test surface 104 by the length of the second gap 118. In such cases, the second gap 118 forms part of the test surface 104 and may constitute the "adjustable" portion of the second adjustable dimension $d_2$. Placing the second gap 118 between the third portion 104c and the second portion 104b of the test surface 104 allows the test surface 104, or the attachment interface included thereon, to create test frames, or receive test pieces, with width-wise dimensions that are not exact multiples of the grid size (e.g., 6 inches). The second gap 118 may be minimized, or eliminated, when the second moveable member 116 is positioned adjacent to, or flush with, the main wall 113. In one example embodiment, a width of the second gap 118 may be adjustable between zero and up to approximately 6 inches.

As shown in FIG. 1, the first adjustable dimension $d_1$ is the sum of two fixed lengths: that of the first portion 104a and the second portion 104b, plus one adjustable length: that of the first gap 114. Similarly, the second adjustable dimension $d_2$ is the sum of two fixed widths: that of the second portion 104b and the third portion 104c, plus one adjustable width: that of the second gap 114. In one exemplary embodiment, the first gap 114 and/or the second gap 118 can be adjusted to any value between 0 and 6 inches. In another exemplary embodiment, the first gap 114 and/or the second gap 118 can be adjusted by increments of $1/16^{th}$ of an inch up to 6 inches. In either case, the length and/or width dimensions of the test surface 104 can be adjusted up to the maximum value of the corresponding gap 114, 118 (e.g., 6 inches). As will be appreciated, larger adjustments to the overall dimensions of the test surface 104 may be achieved by making the maximum value of the first and/or second gaps larger. In embodiments, a maximum value of the first and second gaps 114 and 118 can be selected so that the test piece remains taut while attached to the test surface 104.

Figure 10:
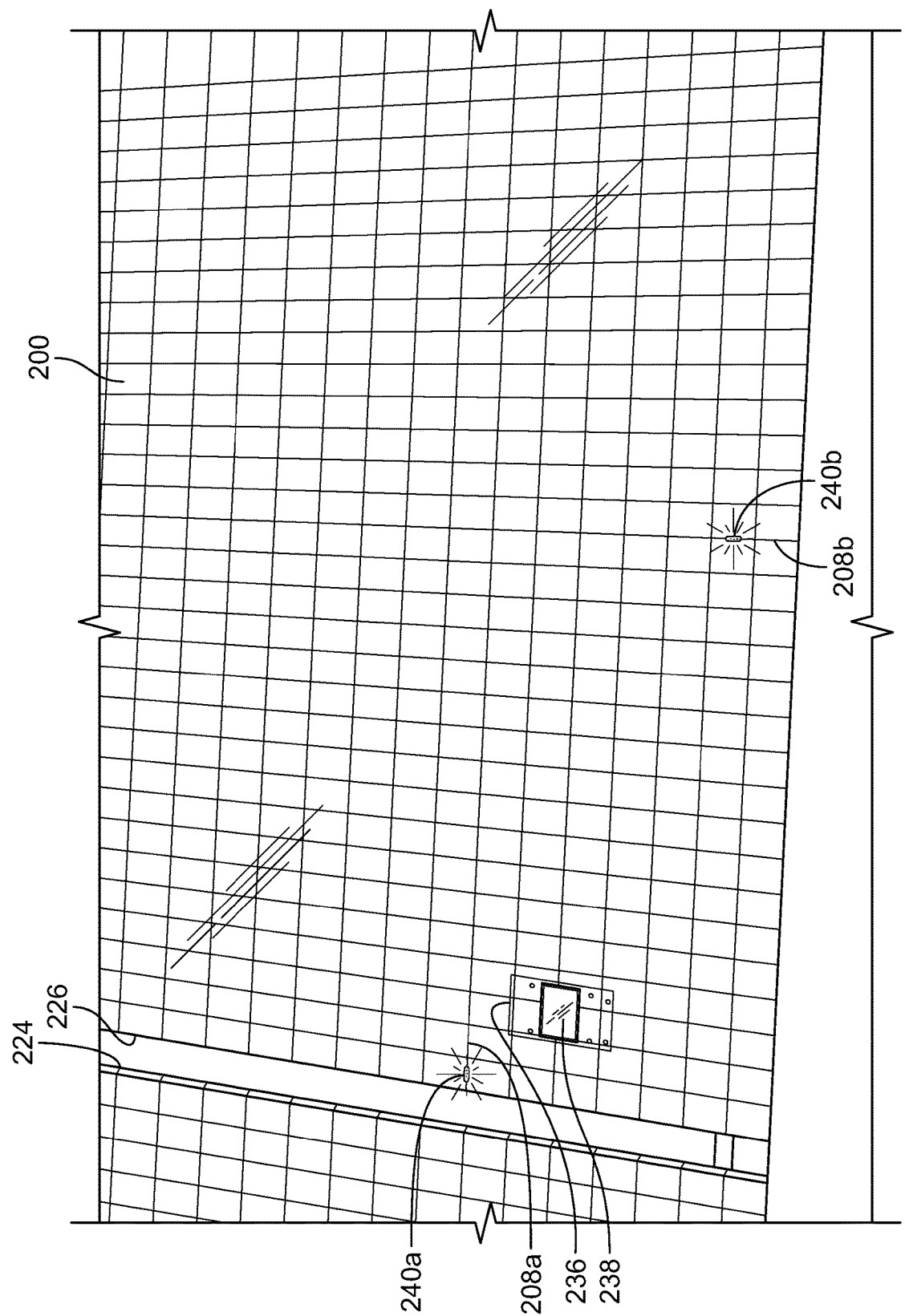
FIG. 10 is a partial view of the wall shown in FIG. 2, illustrating operation of position indicators coupled to the wall, in accordance with embodiments.

FIGS. 9 and 10 illustrate various exemplary components of a test surface adjustment system included on, or attached to, the fabric test wall 200, in accordance with embodiments. Like the test fitting system 100, the fabric test wall 200 includes a lower panel 222 (similar to the first moveable member 112 in FIG. 1), a side panel 224 (similar to the second moveable member 116 shown in FIG. 1), and a central panel 226 (similar to the main wall 113 shown in FIG. 1). According to embodiments, the test surface adjustment system of the fabric test wall 200 also includes a first mechanism 228 (similar to the first mechanism 108) for moving the lower panel 222 relative to the central panel 226 and a second mechanism 230 (similar to the second mechanism 110) for moving the side panel 224 relative to the central panel 226. As shown in FIGS. 8A and 8B, the lower panel 222 includes the bottom channel 218 and the keder rail 220 of the attachment interface included on the fabric test wall 200. Further, as shown in FIG. 6, the side panel 224 includes the vertical track 214 of the attachment interface included on the wall 200.

Referring back to FIG. 9, the test surface adjustment system of the fabric test wall 200 is configured to form a first adjustable gap 232 (similar to the first gap 114 shown in FIG. 1) between the lower panel 222 and the central panel 226 as the lower panel 222 moves away from the central panel 226. Similarly, a second adjustable gap 234 (similar to the second gap 118 shown in FIG. 1) forms between the side panel 224 and the central panel 226 as the side panel 224 moves away from the central panel 226. In embodiments, the first mechanism 228 can be coupled to the lower panel 222 and/or the central panel 226 for creating the first adjustable gap 232, and the second mechanism 230 can be coupled to the side panel 222 and/or the central panel 226 for creating the second adjustable gap 234. For example, the first adjustable gap 232 may be formed by moving the lower panel 222 away from the central panel 226, moving the central panel 226 away from the lower panel 222, or a combination of both movements. Likewise, the second adjustable gap 234 may be formed by moving the side panel 224 away from the central panel 226, moving the central panel 226 away from the side panel 224, or a combination of both movements.

Referring again to FIGS. 1 and 11, in embodiments, the test surface adjustment system 300 further includes a control panel 120 configured for, or capable of, controlling operation of the test surface adjustment system 300 and/or the test fitting system 100, in order to provide automatic adjustment of the test surface dimensions. For example, the control panel 120 can be communicatively coupled to the first mechanism 108 and can include a processor 302 configured to generate instructions for causing the first mechanism 108 to move the first moveable member 112 and/or adjust the first gap 114 by a specified amount or to a specified distance/value. Similarly, the control panel 120 can be communicatively coupled to the second mechanism 110, and the processor 302 can be configured to generate instructions for causing the second mechanism 110 to move the second moveable member 116 and/or adjust the second gap 118 by a specified amount or to a specified distance/value. In the illustrated embodiment, the control panel 120 is coupled to the flat structure 102. In other embodiments, the control panel 120 may be detached from the flat structure 102 and positioned elsewhere on the system 300 or configured as a handheld device that is in wired or wireless communication with the system 300.

In embodiments, the control panel 120 further includes a user interface 122 comprising one or more input devices 304 and/or display devices 306 to allow user interaction with the control panel 120, including receiving an expected size (e.g., length and width dimensions) of a particular test piece or dimensions for a desired test frame, and displaying outputs associated therewith, in accordance with the techniques described herein. For example, the display screen 306 included in the user interface 122 may be used for displaying menu options for navigating a menu interface, control settings, and/or other parameters associated with operation of the fabric test wall 200. In embodiments, the display screen 306 may be a liquid crystal display (LCD), an LED display, a touchscreen, or any other type of display screen. The input devices 304 included in the user interface 122 may include a keyboard, mouse, touchpad, keypad, or any other type of device for receiving user inputs. In some cases, the input devices 304 may include a plurality of menu buttons or the like for navigating menu options presented on the display screen 306 and/or entering information into the control panel 120, including, for example, a size of or dimensions for a particular test piece or test frame In response to receiving particular dimensions via the user interface 122, the control panel 120 can be configured to calculate an adjustment amount for one or more dimensions of the test surface 104 based on a difference between the received dimensions and the current dimensions of the test surface 104. The current dimensions of the test surface 104 may be the original dimensions of the test surface 104, wherein both of the gaps 114 and 118 have substantially zero values, or the last-configured dimensions that were entered and implemented in order to accommodate a prior test piece. The control panel 120 can be configured to instruct the first and/or second mechanisms 108 and 110 to move the first and/or second moveable members 114 and 116, respectively, in order to implement the adjustment dictated by the calculated adjustment amount(s). For example, if the current length of the test surface 104 is longer than a length of the desired test frame, the control panel 120 may instruct the first mechanism 108 to move the first moveable member 112 closer to the main wall 113, or reduce the first gap 114 therebetween, by an amount equal to the difference in length. Similarly, if the current width of the test surface 104 is less than a width of the test frame, the control panel 120 may instruct the second mechanism 110 to move the second moveable member 116 away from the main wall 113, or increase the second gap 118 therebetween, by an amount equal to the difference in width.

FIG. 9 shows an exemplary control panel 236 attached to the fabric test wall 200 for controlling operation of the test surface adjustment system included on the wall 200, in accordance with embodiments. The test surface adjustment system of the wall 200 may be similar to the test surface adjustment system 300. For example, the control panel 236 may be similar to the control panel 120 shown in FIG. 11. As shown in FIG. 9, the control panel 236 includes a user interface 238 (similar to the user interface 122 of FIG. 11) that is configured to display content and enable user entry of commands, numerical values or dimensions, menu selections, and/or other inputs associated with testing the fit of a test piece using the wall 200. For example, the user interface 238 can be configured to receive dimensions for a desired test frame and/or an expected size, including length and width values, for a particular test piece prior to installation of the piece on the wall 200. In one exemplary embodiment, the user interface 238 is a touchscreen capable of displaying menu options and receiving corresponding touch-based inputs. Like the control panel 120 shown in FIG. 11, the control panel 236 may be communicatively coupled to the first mechanism 228 in order to provide instructions to the first mechanism 228 for moving the lower panel 222 and/or adjusting the first adjustable gap 232 in accordance with the adjustments calculated by the processor 302. Similarly, the control panel 236 may be communicatively coupled to the second mechanism 230 in order to provide instructions to the second mechanism 230 for moving the side panel 224 and/or adjusting the second adjustable gap 234 in accordance with the adjustments calculated by the processor 302.

In the illustrated embodiments, the first and second mechanisms 228 and 230 are servo motors electrically coupled to the control panel 236. According to other embodiments, the first and second mechanisms 108 and 110 can be any other type of motor or mechanism capable of receiving and executing commands from the control panel 120. In still other embodiments, the first and second mechanisms 108 and 110 can be manually operated using hand cranks, levers, or motors for adjusting the dimensions of the test surface. In such cases, the control panel 120 may still calculate the amount of adjustment required for each dimension of the test surface, and the user interface 122 may present the adjustment amount as a guide for the user while performing the manual adjustment. In some embodiments, the test fitting system 100 may include more than one mechanism for controlling each adjustable dimension of the test surface 104. For example, as shown in FIG. 2, the fabric test wall 200 includes two mechanisms 228 for adjusting the vertical or length-wise dimension of the test surface. The exact number of mechanisms may vary depending on the size and/or weight of the wall 200, the sizes and/or weights of the panels 222, 224, and 226, and/or the sizes of the gaps 232 and 234.

As shown in FIG. 1, the test surface adjustment system 300 can further include a plurality of position indicators 124 positioned throughout the test surface 104. As shown in FIG. 11, the position indicators 124 can be communicatively coupled to the control panel 120, via the processor 302. According to embodiments, the position indicators 124 can be configured to visually indicate an outline of the desired test frame and/or an expected position of the test piece to assist the user with placement of the test piece on the test surface 104. For example, the control panel 120, or the processor 302, can be configured to determine or select which of the position indicators 124 should be activated based on the expected size and/or orientation of the test frame and/or the fabric piece, or other information received via the user interface 122. The control panel 120 can then generate instructions for activating the selected position indicators 124 and provide the activation instructions thereto. Activation of the selected position indicators 124 can provide a visual marker of where or how the test piece should be attached to the test surface 104.

For example, FIG. 10 depicts an exemplary set of position indicators 240 that are lights (e.g., light emitting diodes or LEDs). While the illustrated embodiment only shows two lights, a first light indicator 240*a* placed adjacent to one of the horizontal channels 208*a* and a second light indicator 240*b* placed adjacent to one of the vertical channels 208*b*, in embodiments, each channel 208*a*, 208*b* of the attachment interface grid 208 may be coupled to a respective one of the light indicators 240. Based on the received dimensions of the test piece, the control panel 236 can determine which horizontal channel 208*a* and which vertical channel 208*b* should be used to attach the edges of the test piece to the wall 200, and can generate activation instructions for each channel accordingly. In some embodiments, the control panel 236 can be configured to activate one corresponding horizontal position indicator 240*a* and one corresponding vertical position indicator 240*b* for each test piece. In response to receiving activation instructions from the control panel 236, the selected light indicators 240 can be configured to illuminate all or a portion of the corresponding channel 208*a*/208*b*. In this manner, the activated light indicators 240 can visually indicate, and guide a user to, a location of the test frame being simulated on the fabric test wall 200.

Though not shown, each channel 208*a*, 208*b* may include one or more position indicators 240, in some embodiments. In the case of multiple indicators 240, the position indicators 240 may be distributed throughout the channel 208*a*/208*b* in order to cover a larger section of the channel 208*a*/208*b*. Though light indicators 240 are shown in FIG. 10, any other type of device capable of communicating with the control panel 236 and visually indicating the position or location of a desired test frame and/or test piece may be used as the position indicators 240/124.

Referring back to FIG. 11, the control panel 120, or the processor 302 therein, can be operatively coupled to the first mechanism 108, the second mechanism 110, and/or the position indicators 124 via a wired connection (e.g., using cables or wires) or a wireless connection (e.g., over a wireless network). The control panel 120 may include circuitry (not shown), in addition to the processor 302 for receiving data from and/or providing control signals to the other components of the system 300. In some embodiments, the control panel 120 may include one or more communication devices, such as, for example, a cable port, a network port, and/or an antenna, to facilitate wireless communication with other devices.

In embodiments, the processor 302 (e.g., data processor) is a hardware device and can comprise one or more of a microprocessor, a microcontroller, a programmable logic array, an application-specific integrated circuit, a logic device, or other electronic device for processing, inputting, outputting, manipulating, storing, or retrieving data. In some embodiments, the data processor 302 can include a central processing unit (CPU) and/or a graphics processing unit (GPU).

As shown in FIG. 11, the control panel 120 further includes a memory 308 (e.g., an electronic memory) coupled to the processor 302. In embodiments, the control panel 120 can be any type of computing device, such as, for example, a tablet or a computer. In some embodiments, the control panel 120 comprises a general purpose computer that is programmed with various programming instructions or modules stored in the memory 308 (e.g., data storage device), or elsewhere. When control panel 120 is in operation, the processor 302 can be configured to execute software stored within memory 308, to communicate data to and from the memory 308, and to generally control operations of the control panel 120 pursuant to the software. In addition, the processor 302 can be configured to communicate data or control signals to, or receive signals from, the user interface 122, the first mechanism 108, the second mechanism 110, the position indicators 124, and/or other components of the system 300.

The memory 308 can comprise one or more of electronic memory, nonvolatile random access memory (e.g., RAM), flip-flops, a computer-writable or computer-readable storage medium, a magnetic or optical data storage device, a magnetic or optical disc drive, a hard disk drive, or other electronic device for storing, retrieving, reading, or writing data. The memory 308 is configured to store executable software, some of which may or may not be unique to the system 300. The software in memory 308 may include one or more separate programs, each comprising an ordered listing of machine readable instructions that, when executed by processor 302, cause the processor 302 to perform various acts and/or implement logical functions. As an example, the software in memory 308 may include a suitable operating system (O/S) and a test fit module 310.

The test fit module 310 may be a portion of the memory 308 that is configured to store software instructions that, when executed by the processor 302, cause the processor 302 to carry out the various test fitting operations described herein. In embodiments, the test fit module 310 can comprise software or program modules for controlling, or generating control instructions for, the first mechanism 108, the second mechanism 110, and/or the position indicators 124 in response to dimensions received via the user interface 122.

The test fit module 310 can also comprise software or program modules for processing inputs received via the user interface 122, calculating certain values based thereon, such as, for example, an expected position of the test frame or test piece on the test surface 104, necessary adjustments to the length and/or width dimensions of the test surface 104 in order to provide a precise fit for the test piece thereon, and the like, as well as identifying one or more channels 208a, 208b for attachment of the test piece and one or more proximity indicators 124 for visually indicating the identified channels 208a, 208b. Other software or program modules stored in the test fit module 310 will become apparent from the below discussion regarding method 400.

In some embodiments, two or more test fitting systems 100 are placed side by side, positioned such that they can be operated independently, in tandem, or in triplicate, etc. Such embodiments would allow simultaneous testing of several panels. Alternatively, the two or more systems may be operated jointly to allow testing of extra large panels. When using two or more systems 100 at a time, the test surface adjustment system 300 associated with each system 100 can be communicatively coupled to one another to facilitate adjustment (or operation) as a single large test system. Other alternative implementations of the test fitting system are contemplated in accordance with the techniques described herein.

Figure 12:
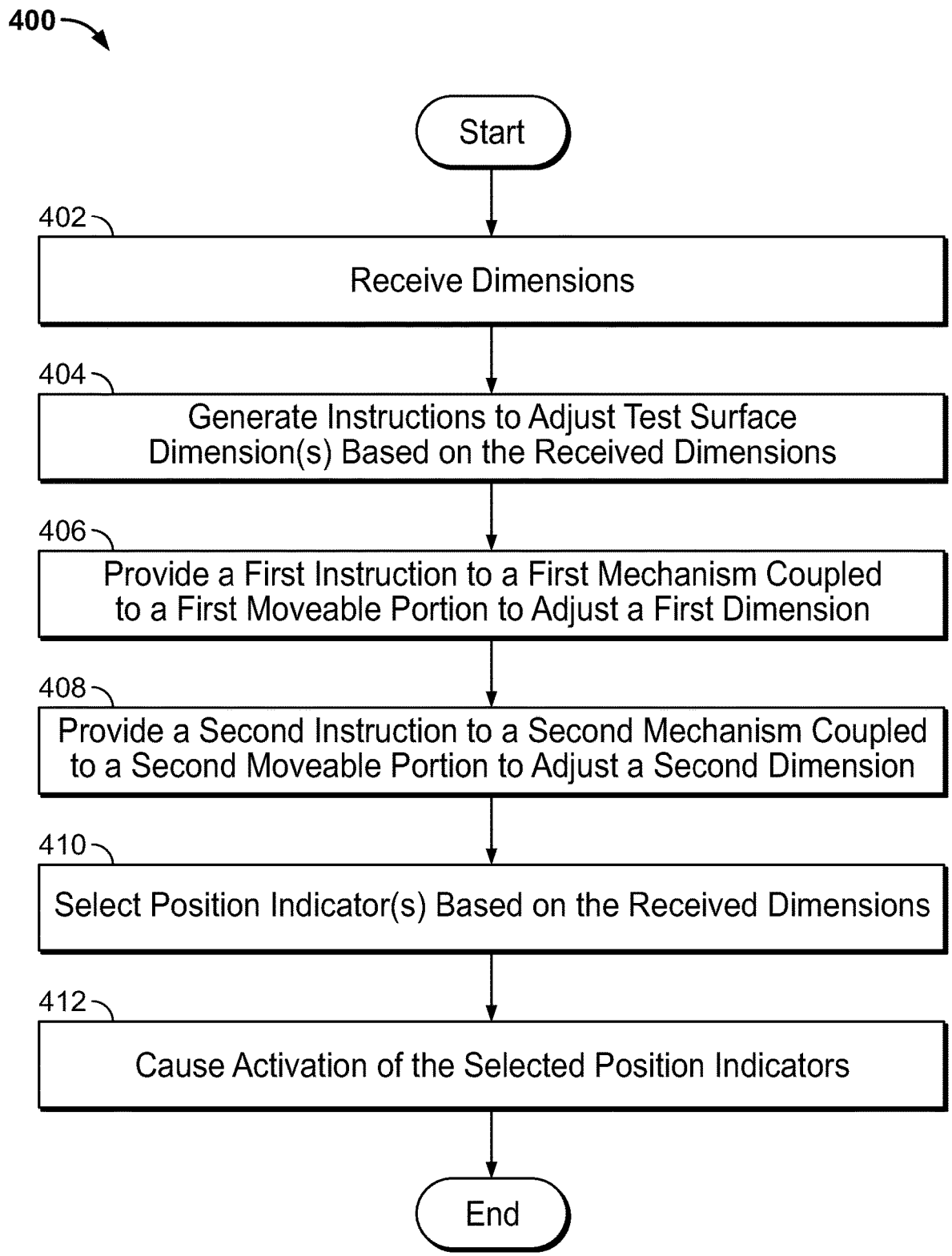
FIG. 12 is a flowchart illustrating an exemplary method of test fitting fabric on a flat structure, in accordance with embodiments.

Referring now to FIG. 12, shown is a flowchart for an example method 400 of testing a fit of a test piece (e.g., fabric sign) on a flat structure (e.g., flat structure 102 shown in FIG. 1), in accordance with embodiments. The method 400 can be carried out by the system 300 shown in FIG. 11, or more specifically, through interactions between various components of the system 300 that are facilitated by software executing on one or more electronic data processors associated with said components. For example, the control panel 120 may interact with the first mechanism 108, the second mechanism 110, and in some cases, the position indicators 124, to carry out the operations of the method 400, and all or a portion of the method 400 can be implemented in software (such as, e.g., the test fit module 310 shown in FIG. 11) that is executable by the data processor 302 and stored in the memory or data storage device 308. Accordingly, in the following paragraphs, the method 400 will be described with reference to the components of the test surface adjustment system 300, as well as the components of the test fitting system 100 which includes the system 300.

In embodiments, the method 400 can begin at step 402 with the processor 302 and/or test fit module 310 receiving, from the user interface 122, one or more inputs comprising dimensions associated with a test piece. For example, the dimensions can be an expected size of the test piece (e.g., fabric sign) being tested on the fabric test wall, or a set of dimensions for the test frame that is required to test the fabric. The one or more inputs can include a length value, a width value, and in some cases, an orientation value (e.g., horizontal orientation or vertical orientation). At step 404, the processor 302 and/or the test fit module 310 generates instructions for adjusting one or more dimensions of the test surface based on the received dimensions. At step 406, the processor 302 and/or the test fit module 310 provides a first one of the instructions to the first mechanism 108, which is coupled to the first moveable portion 112 of the flat structure 102, for causing automatic adjustment of the first adjustable dimension $d_1$ of the test surface 104.

In embodiments, generating instructions at step 404 can include calculating a first adjustment amount for the length of the second sidewall 106c based on the received dimensions for the test frame and/or test piece, and configuring the first instruction to cause the first mechanism 108 to move the first moveable member 112 by the first adjustment amount. In some embodiments, calculating the first adjustment amount includes calculating a difference between the length of the second sidewall 106c and a length value included in the received dimensions.

The method 400 may also include at step 408, providing a second one of the instructions to the second mechanism 110, which is coupled to the second moveable portion 116 of the flat structure 102 for causing automatic adjustment of the second adjustable dimension $d_2$ of the test surface. In embodiments, generating instructions at step 406 can include calculating a second adjustment amount for the width of the second sidewall 106c based on the received dimensions of the test frame or piece, and configuring the second instruction to cause the second mechanism 110 to move the second moveable member 116 by the second adjustment amount. In some embodiments, calculating the second adjustment amount includes calculating a difference between the width of the second sidewall 106c and a width value included in the received dimensions.

In some embodiments, the method 400 also includes step 410, where the processor 302 and/or the test fit module 310 select one or more of the position indicators 124 positioned adjacent to the test surface 104, and step 412, where the processor 302 and/or the test fit module 310 cause activation of the selected position indicator(s) 124, thereby visually indicating the expected position of the test frame and/or test piece. As an example, selecting one or more position indicators 124 in step 410 may include determining an expected position of the test piece prior to placement on the test surface 104, and selecting the one or more position indicators 124 based on a proximity of the one or more position indicators to the expected position. In embodiments, determining an expected position of the test piece, as part of step 410, can include determining an orientation of the test piece on the test surface based on the dimensions received at step 402. The orientation can be selected from a group consisting of a horizontal (or lengthwise) orientation and a vertical (or upright) orientation. In some embodiments, the orientation value may be selected so that oblong test pieces or test frames are positioned with the longer side along the horizontal axis of the wall and the short side along the vertical axis of the wall. For example, the horizontal orientation may be selected if the received dimensions indicate that the length value for the test piece or test frame is at least twice the width value for the same. As another example, the vertical orientation may be selected if the received dimensions indicate that the width value for the test piece or frame is greater than the length value for the same.

Thus, improved systems and methods for testing a fit of a fabric piece or other flexible test piece are described herein. The techniques include securely attaching the test piece to a vertical wall structure that is sized to fit even the largest of signs or banners, and providing adjustable sections on the vertical wall structure that are capable of precisely adjusting one or more dimensions of the test surface in order to provide a test frame that closely matches the expected dimensions of the fabric piece.

In certain embodiments, the process descriptions or blocks in the figures, such as FIG. 12, can represent modules, segments, or portions of code which include one or more executable instructions for implementing specific logical functions or steps in the process. Any alternate implementations are included within the scope of the embodiments described herein, in which functions may be executed out of order from that shown or discussed, including substantially concurrently or in reverse order, depending on the functionality involved, as would be understood by those having ordinary skill in the art.

It should be emphasized that the above-described embodiments, particularly, any "preferred" embodiments, are possible examples of implementations, merely set forth for a clear understanding of the principles of the invention. Many variations and modifications may be made to the above-described embodiment(s) of the invention without substantially departing from the spirit and principles of the invention. All such modifications are intended to be included herein within the scope of this disclosure and protected by the following claims.

The invention claimed is:

1. A system for test fitting fabric, comprising:
a flat structure comprising a test surface defined by four sidewalls and an interface configured to attach the fabric to the test surface, the four sidewalls including a first sidewall and a second sidewall substantially perpendicular to the first sidewall, and the test surface comprising a first adjustable dimension substantially parallel to the second sidewall and a second adjustable dimension substantially parallel to the first sidewall;
a user interface configured to receive one or more inputs for adjusting the first adjustable dimension and the second adjustable dimension;
a first mechanism configured to, in response to the one or more inputs, automatically move the first sidewall to adjust the first adjustable dimension; and
a second mechanism configured to, in response to the one or more inputs, automatically move the second sidewall to adjust the second adjustable dimension.

2. The system of claim 1, wherein the flat structure further comprises a first moveable member comprising the first sidewall and a first portion of the test surface, the first mechanism being configured to move the first moveable member relative to a second portion of the test surface in order to adjust the first adjustable dimension.

3. The system of claim 2, wherein the flat structure further comprises a second moveable member comprising the second sidewall and a third portion of the test surface, the second mechanism being configured to move the second moveable member relative to the second portion of the test surface in order to adjust the second adjustable dimension.

4. The system of claim 3, further comprising a frame for supporting the flat structure, wherein the second portion of the test surface is fixedly attached to the frame.

5. The system of claim 1, wherein the interface includes a grid formed from a plurality of horizontal and vertical channels, each channel being configured to receive an edge of the fabric.

6. The system of claim 5, wherein each channel is configured to receive a silicon gasket attached to the edge of the fabric.

7. The system of claim 1, further comprising a processor communicatively coupled to the user interface and the first and second mechanisms, the processor generating instructions for the first and second mechanisms based on the one or more inputs received via the user interface.

8. The system of claim 1, further comprising a plurality of position indicators coupled to the flat structure, each position indicator in communication with the user interface and configured to indicate an expected position of the fabric on the interface in response to the one or more inputs.

9. The system of claim 1, wherein each of the first mechanism and the second mechanism is a servo-motor.

10. A method of test fitting fabric on a flat structure comprising a test surface, the flat structure being included in a system comprising a processor and a user interface, the method comprising:
receiving, via the user interface, dimensions associated with a test piece;
generating, using the processor, instructions for adjusting one or more dimensions of the test surface based on the received dimensions; and
providing a first one of the instructions to a first mechanism coupled to a first moveable portion of the flat structure for causing automatic adjustment of a first dimension of the test surface.

11. The method of claim 10, wherein the first moveable portion includes a first sidewall of the flat structure, and the first dimension of the test surface is a length of a second sidewall of the flat structure, the first sidewall being perpendicular to the second sidewall.

12. The method of claim 11, wherein generating instructions includes:
calculating a first adjustment amount for the length of the second sidewall based on the received dimensions, and
configuring the first instruction to cause the first mechanism to move the first moveable portion by the first adjustment amount.

13. The method of claim 12, wherein calculating the first adjustment amount includes calculating a difference between the length of the second sidewall and a length included in the received dimensions.

14. The method of claim 11, further comprising providing a second one of the instructions to a second mechanism coupled to a second moveable portion of the flat structure for causing automatic adjustment of a second dimension of the test surface.

15. The method of claim 14, wherein the second moveable portion of the flat structure includes the first sidewall of the flat structure, and the second dimension of the test surface is a width of the first sidewall of the flat structure.

16. The method of claim 15, wherein generating instructions includes:
calculating a second adjustment amount for the width of the first sidewall based on the received dimensions, and
configuring the second instruction to cause the second mechanism to move the second moveable portion by the second adjustment amount.

17. The method of claim 16, wherein calculating the second adjustment amount includes calculating a difference between the width of the first sidewall and a width included in the received dimensions.

18. The method of claim 10, wherein the system further comprises a plurality of position indicators positioned adjacent to the test surface, the method further comprising:
determining, using the processor, an expected position of the fabric on the test surface based on the received dimensions;
selecting, using the processor, one or more of the position indicators based on a proximity of the one or more position indicators to said expected position; and
causing the one or more position indicators to activate, thereby visually indicating the expected position of the fabric.

19. The method of claim 18, wherein determining the expected position of the fabric includes determining an orientation of the fabric on the test surface based on the received dimensions, the orientation being selected from a group consisting of horizontal orientation and vertical orientation.

\* \* \* \* \*